United States Patent
Happ et al.

(10) Patent No.: US 6,544,219 B2
(45) Date of Patent: Apr. 8, 2003

(54) CATHETER FOR PLACEMENT OF THERAPEUTIC DEVICES AT THE OSTIUM OF A BIFURCATION OF A BODY LUMEN

(75) Inventors: Dorrie M. Happ, San Jose, CA (US);
Virgilda Torate, Fremont, CA (US);
Stephen J. Bigus, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/738,577

(22) Filed: Dec. 15, 2000

(65) Prior Publication Data

US 2002/0077591 A1 Jun. 20, 2002

(51) Int. Cl.⁷ .............................................. A61M 29/00
(52) U.S. Cl. .................... 604/96.01; 604/104; 604/192; 604/284; 604/528
(58) Field of Search ............................... 604/96.01, 104, 604/191, 192, 194, 264, 284, 523, 528

(56) References Cited

U.S. PATENT DOCUMENTS

| 2,845,959 A | 8/1958 | Sidebotham |
| 2,978,787 A | 4/1961 | Liebig |
| 2,990,605 A | 7/1961 | Demsyk |

(List continued on next page.)

FOREIGN PATENT DOCUMENTS

| EP | 0 461 791 A1 | 12/1991 |
| EP | 0 466 518 A3 | 1/1992 |
| EP | 0 747 020 A2 | 12/1996 |
| EP | 0 804 907 A2 | 11/1997 |
| FR | 0 673 843 | 9/1992 |
| FR | 2 737 969 | 2/1997 |
| SU | 1217402 A | 3/1986 |
| SU | 1318235 A1 | 6/1987 |
| SU | 1389778 A2 | 4/1988 |
| SU | 1457921 A1 | 2/1989 |

(List continued on next page.)

OTHER PUBLICATIONS

Lawrence, David D., Jr., M.D., et al., *Percutaneous Endovascular Graft: Experimental Evaluation*, Radiology, vol. 163, No. 2, pp. 357–360 (1987).

Yoshioka, Tetsuya, et al., *Self–Expanding Endovascular Graft: An Experimental Study in Dogs*, Radiology, vol. 170, pp. 673–676 (1989).

(List continued on next page.)

*Primary Examiner*—Charles G. Preay
*Assistant Examiner*—John F. Belena
(74) *Attorney, Agent, or Firm*—Fulwider Patton Lee & Utecht, LLP (57) ABSTRACT

The catheter assembly includes an expandable member mounted to the distal end of a placement catheter, for delivery of a therapeutic device in one of the branch vessels of a bifurcated vessel. The catheter assembly includes lumens for a tracking guide wire and a positioning guide member for placement of the therapeutic device. The therapeutic device is mounted on the expandable member, the tracking guide wire is placed into the target branch vessel, and the placement catheter is then introduced over the tracking guide wire. A positioning guide member is introduced through the catheter, extended through an exit port in the catheter proximal to the expandable member, and then placed in another branch vessel of the bifurcation. The placement catheter then is advanced until the positioning guide member engages the vessel carina between the branch vessels, and the therapeutic device then may be placed accurately in the target branch vessel. In another form of the catheter assembly, a secondary catheter member is mounted to the placement catheter and adapted to receive the positioning guide member for placement of the positioning guide member in the vessel branch not to be treated. An elongated angle member is mounted to the secondary catheter member for engagement with the vessel carina.

15 Claims, 2 Drawing Sheets

U.S. PATENT DOCUMENTS

| | | |
|---|---|---|
| 3,096,560 A | 7/1963 | Liebig |
| 3,142,067 A | 7/1964 | Liebig |
| 3,657,744 A | 4/1972 | Ersek |
| 3,908,662 A | 9/1975 | Razgulov et al. |
| 3,945,052 A | 3/1976 | Liebig |
| 4,041,931 A | 8/1977 | Elliot et al. |
| 4,047,252 A | 9/1977 | Liebig et al. |
| 4,061,134 A | 12/1977 | Samuels et al. |
| 4,108,161 A | 8/1978 | Samuels et al. |
| 4,140,126 A | 2/1979 | Choudhury |
| 4,193,137 A | 3/1980 | Heck |
| 4,202,349 A | 5/1980 | Jones |
| 4,214,587 A | 7/1980 | Sakura, Jr. |
| 4,517,687 A | 5/1985 | Liebig et al. |
| 4,560,374 A | 12/1985 | Hammerslag |
| 4,562,596 A | 1/1986 | Kornberg |
| 4,577,631 A | 3/1986 | Kreamer |
| 4,617,932 A | 10/1986 | Kornberg |
| 4,652,263 A | 3/1987 | Herweck et al. |
| 4,693,249 A | 9/1987 | Schenck et al. |
| 4,728,328 A | 3/1988 | Hughes et al. |
| 4,732,152 A | 3/1988 | Wallsten et al. |
| 4,739,762 A | 4/1988 | Palmaz |
| 4,787,899 A | 11/1988 | Lazarus |
| 4,793,348 A | 12/1988 | Palmaz |
| 4,795,458 A | 1/1989 | Regan |
| 4,795,465 A | 1/1989 | Marten |
| 4,830,003 A | 5/1989 | Wolff et al. |
| 4,872,874 A | 10/1989 | Taheri |
| 4,878,906 A | 11/1989 | Lindemann et al. |
| 4,892,539 A | 1/1990 | Koch |
| 4,950,227 A | 8/1990 | Savin et al. |
| 4,969,890 A | 11/1990 | Sugita et al. |
| 4,969,896 A | 11/1990 | Shors |
| 4,994,071 A | 2/1991 | MacGregor |
| 5,047,050 A | 9/1991 | Arpesani |
| 5,104,399 A | 4/1992 | Lazarus |
| 5,108,424 A | 4/1992 | Hoffman, Jr. et al. |
| 5,127,919 A | 7/1992 | Ibrahim et al. |
| 5,135,536 A | 8/1992 | Hillstead |
| 5,156,619 A | 10/1992 | Ehrenfeld |
| 5,178,630 A | 1/1993 | Schmitt |
| 5,178,634 A | 1/1993 | Martinez |
| 5,197,976 A | 3/1993 | Herweck et al. |
| 5,197,977 A | 3/1993 | Hoffman, Jr. et al. |
| 5,304,220 A | 4/1994 | Maginot |
| 5,316,023 A | 5/1994 | Palmaz et al. |
| 5,360,443 A | 11/1994 | Barone et al. |
| 5,443,497 A | 8/1995 | Venbrux |
| 5,443,498 A | 8/1995 | Fontaine |
| 5,456,712 A | 10/1995 | Maginot |
| 5,507,769 A | 4/1996 | Marin et al. |
| 5,514,154 A | 5/1996 | Lau et al. |
| 5,522,880 A | 6/1996 | Barone et al. |
| 5,527,355 A | 6/1996 | Ahn |
| 5,562,724 A | 10/1996 | Vorwerk et al. |
| 5,562,726 A | 10/1996 | Chuter |
| D376,011 S | 11/1996 | Nunokawa |
| 5,571,167 A | 11/1996 | Maginot |
| 5,571,170 A | 11/1996 | Palmaz et al. |
| 5,571,171 A | 11/1996 | Barone et al. |
| 5,571,173 A | 11/1996 | Parodi |
| 5,575,817 A | 11/1996 | Martin |
| 5,578,071 A | 11/1996 | Parodi |
| 5,578,072 A | 11/1996 | Barone et al. |
| 5,591,228 A | 1/1997 | Edoga |
| 5,591,229 A | 1/1997 | Parodi |
| 5,603,721 A | 2/1997 | Lau et al. |
| 5,609,627 A | 3/1997 | Goicoechea et al. |
| 5,613,980 A | 3/1997 | Chauhan |
| 5,617,878 A | 4/1997 | Taheri |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,649,952 A | 7/1997 | Lam |
| 5,669,924 A | 9/1997 | Shaknovich |
| 5,676,696 A | 10/1997 | Marcade |
| 5,676,697 A | 10/1997 | McDonald |
| 5,683,450 A | 11/1997 | Goicoechea et al. |
| 5,683,452 A | 11/1997 | Barone et al. |
| 5,683,453 A | 11/1997 | Palmaz |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,517 A | 12/1997 | Marin et al. |
| 5,709,713 A | 1/1998 | Evans et al. |
| 5,713,917 A | 2/1998 | Leonhardt et al. |
| 5,718,734 A | 2/1998 | Goicoechea et al. |
| 5,720,735 A | 2/1998 | Dorros |
| 5,735,893 A | 4/1998 | Lau et al. |
| 5,749,825 A | 5/1998 | Fischell et al. |
| 5,755,734 A | 5/1998 | Richter et al. |
| 5,755,735 A | 5/1998 | Richter et al. |
| 5,755,771 A | 5/1998 | Penn et al. |
| 5,776,180 A | 7/1998 | Goicoechea et al. |
| 5,782,906 A | 7/1998 | Marshall et al. |
| 5,800,508 A | 9/1998 | Goicoechea et al. |
| 5,800,520 A | 9/1998 | Fogarty et al. |
| 5,827,320 A | 10/1998 | Richter et al. |
| 5,879,382 A | 3/1999 | Boneau |
| 5,893,887 A | 4/1999 | Jayaraman |
| 5,895,407 A | 4/1999 | Jayaraman |
| 5,902,332 A | 5/1999 | Schatz |
| 5,916,234 A | 6/1999 | Lam |
| 5,916,263 A | 6/1999 | Goicoechea et al. |
| 5,919,225 A | 7/1999 | Lau et al. |
| 5,921,995 A | 7/1999 | Kleshinski |
| 5,938,696 A | 8/1999 | Goicoechea et al. |
| 5,954,693 A | 9/1999 | Barry |
| 5,972,017 A | 10/1999 | Berg et al. |
| 5,976,155 A | 11/1999 | Foreman et al. |
| 6,030,413 A | 2/2000 | Lazarus |
| 6,030,414 A | 2/2000 | Taheri |
| 6,030,415 A | 2/2000 | Chuter |
| 6,033,434 A | 3/2000 | Borghi |
| 6,033,435 A | 3/2000 | Penn et al. |
| 6,039,754 A | 3/2000 | Caro |
| 6,048,361 A | 4/2000 | Von Oepen |
| 6,051,020 A | 4/2000 | Goicoechea et al. |
| 6,051,021 A | 4/2000 | Frid |
| 6,059,810 A | 5/2000 | Brown et al. |
| 6,066,168 A | 5/2000 | Lau et al. |
| 6,086,610 A | 7/2000 | Duerig et al. |
| 6,129,738 A * | 10/2000 | Lashinski et al. ...... 604/101.04 |
| 6,221,090 B1 * | 4/2001 | Wilson ............... 606/194 |
| 6,258,073 B1 * | 7/2001 | Mauch ............... 604/284 |
| 6,355,061 B1 * | 3/2002 | Quiachon et al. ........ 604/6.01 |
| 6,361,544 B1 * | 3/2002 | Wilson et al. .......... 604/101.1 |
| 6,361,555 B1 * | 3/2002 | Wilson ............... 606/108 |
| 6,447,501 B1 * | 9/2002 | Solar et al. .......... 604/528 |

FOREIGN PATENT DOCUMENTS

| | | |
|---|---|---|
| SU | 1482714 A2 | 5/1989 |
| WO | WO 95/16406 | 6/1995 |
| WO | WO 95/21592 | 8/1995 |
| WO | WO 96/23455 | 8/1996 |
| WO | WO 96/24306 | 8/1996 |
| WO | WO 96/24308 | 8/1996 |
| WO | WO 96/34580 | 11/1996 |

| | | |
|---|---|---|
| WO | WO 97/07752 | 3/1997 |
| WO | WO 97/15346 | 5/1997 |
| WO | WO 97/16217 | 5/1997 |
| WO | WO 97/41803 | 11/1997 |
| WO | WO 97/45073 | 12/1997 |
| WO | WO 98/36709 | 8/1998 |
| WO | WO 99/04726 | 2/1999 |

OTHER PUBLICATIONS

Mirich, David, M.D., et al., *Percutaneously Placed Endovascular Grafts for Aortic Aneurysms: Feasibility Study*, Radiology, vol. 170, No. 3, Part 2, pp. 1033–1037 (1989).

Parodi, J.C., M.D., et al., *Transfemoral Intraluminal Graft Implantation for Abdominal Aortic Aneurysms*, Annals of Vascular Surgery, vol. 5, No. 6, pp. 491–499 (1991).

Chuter, Timothy A.M., et al., *Transfemoral Endovascular Aortic Graft Placement*, Journal of Vascular Surgery, pp. 185–196 (Aug. 1993).

Bard XT Catina Bifurcate Stent (Brochure) (Undated).

* cited by examiner

CATHETER FOR PLACEMENT OF THERAPEUTIC DEVICES AT THE OSTIUM OF A BIFURCATION OF A BODY LUMEN

BACKGROUND OF THE INVENTION

1. Field of the Invention

This invention relates generally to catheters for placement of a therapeutic device at a bifurcation of a body lumen, and more particularly concerns a catheter adapted to utilize two guide wires for precise placement of a therapeutic device with respect to the ostium of a vascular bifurcation for repairing lesions at the vascular bifurcation.

2. Description of Related Art

Stents are typically implanted within a vessel in a contracted state and expanded when in place in the vessel in order to maintain patency of the vessel to allow fluid flow through the vessel. Implantation of such stents is commonly accomplished by mounting the stent on the balloon portion of a catheter, positioning the stent in a body lumen, and expanding the stent to an expanded state by inflation of a balloon within the stent. The stent can then be left in place by deflating the balloon and removing the catheter. An alternate approach is to utilize a self-expanding stent that is introduced in a collapsed state, so that when properly positioned, a retaining sheath can be withdrawn, allowing the stent to expand into position.

A bifurcated stenosis typically can occur in the carotid or coronary arteries at the carina between adjoining arterial branches and around the ostia of the adjoining arterial branches. A bifurcated stenosis can also occur in other bifurcated body lumens, such as in the renal and iliac arteries, for example. Particularly at a vascular bifurcation, lesions may form along the side walls of the blood vessel and at the carina of the bifurcation, contributing to stenosis of the main branch and side branch of the bifurcation, interfering with the normal rheology of flow at the bifurcation, and contributing to the formation of thrombosis.

The accurate, precise delivery of stents at a treatment site of a bifurcated blood vessel has heretofore presented numerous problems. Current methods of placing a stent rely heavily on fluoroscopic equipment and the physician's ability to accurately visualize and place a stent. This technique is relatively effective in a straight or non-branched anatomy. However, it has been found that the precise positioning of a stent in a specific location such as at the carina of a vascular bifurcation using two dimensional images of a three dimensional vascular bifurcation can pose significant problems for the practitioner. While visualizing the delivery system itself is not a critical issue, holding and accurately placing a stent within 1 mm of an ostium of a side branch vessel at a vascular bifurcation can be a tremendous challenge.

In one method for delivery of a stent at a treatment site of a bifurcated blood vessel, a main vessel stent is implanted at the bifurcation across a side branch, and the structure of main vessel stent must be spread apart sufficiently to form an opening to the side branch vessel for a catheter with a stent for the side branch to be delivered through the opening. The portion of the structure of the main vessel stent to be spread apart is typically selected by trial and error by crossing and recrossing the structure of the main vessel stent with a wire. In addition, the aperture created through the main vessel stent may not provide a clear opening and can create a major distortion in the surrounding structure of the stent.

A need continues to exist for a system for accurately and precisely placing a stent within a side branch portion of a bifurcated blood vessel at the ostium of the side branch vessel to be treated, to minimize the unstented portion of a lesion at the vascular bifurcation, without blocking flow to an unstented side branch of the bifurcation of the blood vessel to be treated. The present invention solves these and other problems, as will be shown.

SUMMARY OF THE INVENTION

Briefly, and in general terms, the present invention provides for an ostial placement catheter assembly and a method for placing a therapeutic device with the catheter assembly, permitting improved accuracy and decreased variability in positioning of a therapeutic device such as a graft or stent at an ostium of a bifurcation of a body lumen, by providing a mechanical stop, allowing the graft or stent to be automatically positioned at the ostium of the bifurcation. The ostial placement catheter assembly and method of the invention can also reduce the amount of time needed to place the stent. While the invention can be used in treatment of vascular bifurcations such as can occur in the carotid or coronary arteries, the invention can also be used in treatment of other vascular bifurcations such as at the renal or iliac arteries, for example, or in treatment of other bifurcated body lumens.

The invention accordingly provides for a catheter assembly for placement of a therapeutic device for treatment of a patient's bifurcated body lumen, such as a bifurcated blood vessel, having a main vessel portion, a plurality of branch vessels extending from the main vessel portion, and a vessel carina between the branch vessels. The catheter assembly includes a placement catheter, with an expandable member mounted adjacent to the distal end of the placement catheter. The placement catheter includes means for inflating and deflating the expandable member, for delivery of a therapeutic device mounted onto the expandable member in one of the branch vessels. The catheter assembly typically includes an adapter hub which provides access to an inflation/deflation lumen. A tracking guide wire lumen within at least a portion of the placement catheter is adapted to receive a tracking guide wire for slidable movement within the tracking guide wire lumen, and a positioning guide member lumen within at least a portion of the placement catheter, having an exit port in the catheter proximal to the expandable member, is adapted to receive a positioning guide member for slidable movement within the positioning guide member lumen.

Figure 2:
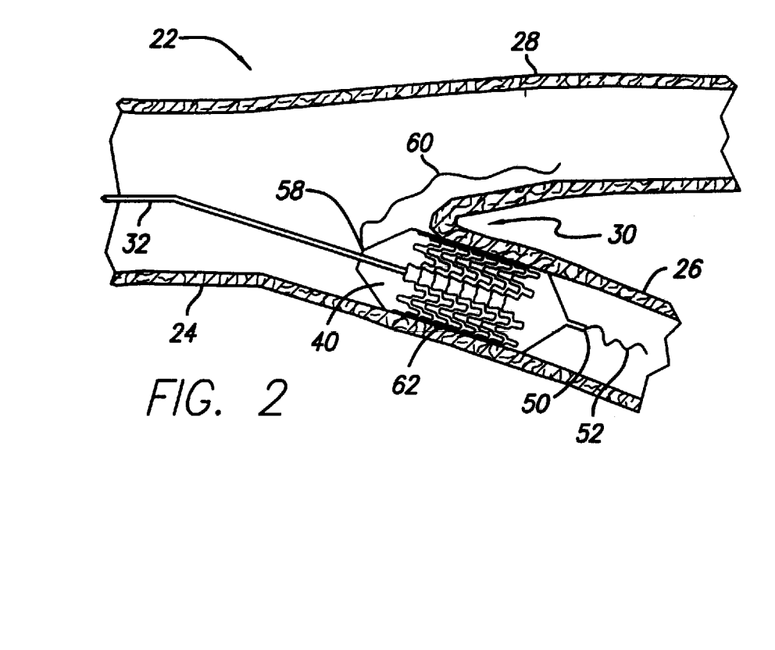
FIG. 2 is a schematic diagram illustrating placement of a therapeutic device with the ostial placement catheter assembly of FIG. 1.

The present invention also provides for a method for placement of a therapeutic device for treatment of a patient's bifurcated body lumen, such as a bifurcated vessel, having a main vessel portion, a plurality of branch vessels extending from the main vessel portion, and a vessel carina between the branch vessels. The method involves the steps of providing a placement catheter of the first preferred embodiment, and mounting a therapeutic device on the expandable member for placement in a target branch vessel. The distal end of a tracking guide wire is placed into the target branch vessel, the placement catheter is introduced over the tracking guide wire through the tracking guide wire lumen, and a positioning guide member is introduced into the positioning guide member lumen from the proximal end of the catheter. The positioning guide member remains hidden inside the positioning guide member lumen during tracking of the target vessel. Near the target vessel, the distal end of the positioning guide member is extended through the exit port in the catheter proximal to or proximally adjacent to the expandable member, and is placed in another branch vessel. The placement catheter is then advanced distally in the main vessel until the positioning guide member engages the vessel carina between the branch vessels, and the therapeutic device is placed in the target branch vessel, as is illustrated in FIG. 2.

In a second presently preferred embodiment, the invention provides for a catheter assembly for placement of a therapeutic device for treatment of a patient's bifurcated body lumen, such as a bifurcated blood vessel, having a main vessel portion, a plurality of branch vessels extending from the main vessel portion, and a vessel carina between the branch vessels. The catheter assembly includes a placement catheter, with an expandable member mounted to the distal end of the placement catheter, and means for inflating and deflating the expandable member. The catheter assembly typically includes an adapter hub which provides access to an inflation/deflation lumen. The expandable member is adapted for mounting and delivery of a therapeutic device in one of the branch vessels. A tracking guide wire lumen within at least a portion of the placement catheter is adapted to receive a tracking guide wire for slidable movement within the tracking guide wire lumen, and a positioning guide member lumen within at least a portion of the placement catheter, and having an exit port in the catheter proximal to the expandable member, is adapted to receive a positioning guide member for slidable movement within the positioning guide member lumen.

The second embodiment of the catheter assembly includes a secondary catheter member mounted to the placement catheter and including a positioning guide member lumen connected in communication with the positioning guide member lumen of the placement catheter, with the positioning guide member lumen of the secondary catheter member adapted to receive the positioning guide member for slidable movement within the positioning guide member lumen of the secondary catheter member. An elongated angle member is mounted to the secondary catheter member, and is adapted to extend between and to be retained by the therapeutic device mounted to the expandable member, between the therapeutic device and the expandable member, so as to form an arch in the elongated angle member between the ends of the elongated angle member and proximal to the therapeutic device. In one currently preferred aspect, one end of the elongated angle member is mounted adjacent to the distal end of the secondary catheter member, and the other end of the elongated angle member is mounted to the placement catheter distal to the expandable member. In another presently preferred aspect means are provided for coupling and uncoupling the distal end of the secondary catheter member to the distal end of the placement catheter distal to the expandable member, and in a currently preferred embodiment the means for coupling and uncoupling includes an annular coupling member connected to the distal end of the placement catheter and adapted to receive the distal end of the positioning guide member.

In the method of placement of a therapeutic device utilizing the catheter assembly of the second preferred embodiment, the distal end of a tracking guide wire is placed into the target branch vessel, and is positioned at a treatment site using standard techniques. The placement catheter is introduced over the tracking guide wire through the tracking guide wire lumen. In a preferred embodiment, an elongated guide member, such as the positioning guide member or another elongated guide member such as a standard guide wire or other type of elongated member, passes through an annular coupling member connected to the distal end of the placement catheter thereby coupling them together. Once the tracking guide wire and elongated guide member are correctly positioned, the catheter is advanced to the treatment site over the tracking wire. The distal end of the secondary catheter member is uncoupled from the distal end of the placement catheter. The positioning guide member is positioned in the alternate, non-treated leg of the bifurcation, and the catheter is advanced over both the tracking guide wire and the positioning guide member until the elongated angle member engages the vessel carina between the branch vessels. The therapeutic device can then be placed in the target branch vessel.

Figure 5:
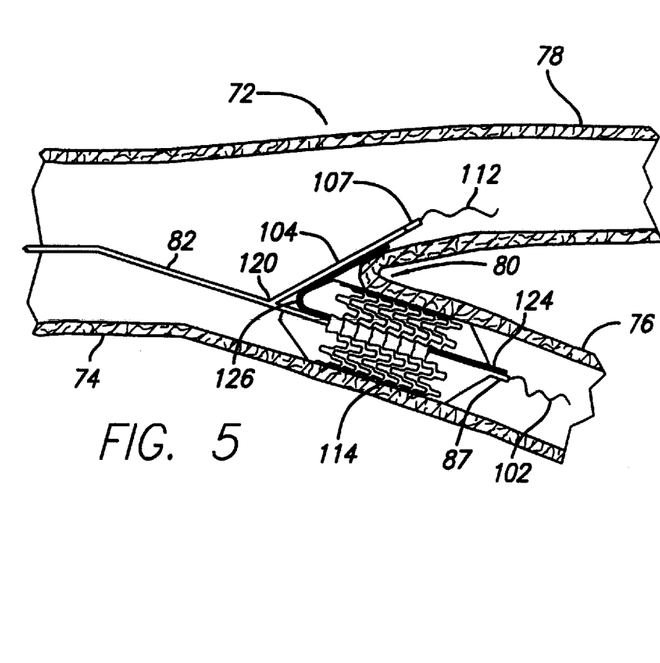
FIG. 5 is a schematic diagram illustrating placement of a therapeutic device with the ostial placement catheter assembly of FIG. 3.

Alternatively, if the tips are not to be bound, a positioning guide member can be introduced through the positioning guide member lumen. In this case, typically the positioning guide member will be advanced until the tip is just proximal to the exit port of the secondary catheter member. The placement catheter is introduced over the tracking guide wire through the tracking guide wire lumen, and the distal end of the positioning guide member is then advanced through the positioning guide member lumen and through the secondary catheter member into the main branch vessel. The placement catheter is advanced distally with a tip in each vessel of the bifurcation until the elongated angle member engages the vessel carina between the branch vessels, and the therapeutic device can then be placed in the target branch vessel as is illustrated in FIG. 5.

As used herein, the terms "proximal" and "proximal direction" when used with respect to the invention are intended to mean moving away from or out of the patient, and the terms "distal" and "distal direction" when used with respect to the invention are intended to mean moving toward or into the patient. These definitions will apply with reference to apparatus, such as catheters, guide wires, and stents. When used with reference to body lumens, such as blood vessels, the terms "proximal" and "proximal direction" are intended to mean closer to the aorta; the terms "distal" and "distal direction" are intended to mean farther from the aorta; and with respect to a bifurcated body lumen in general, the terms "distal" and "distal direction" are intended to mean in the direction in which the branching from the parent lumen to the branched lumens occurs.

These and other aspects and advantages of the invention will become apparent from the following detailed description and the accompanying drawings, which illustrate by way of example the features of the invention.

DETAILED DESCRIPTION OF THE PREFERRED EMBODIMENTS

In treating branch vessels and the region at the ostium of the branch vessels that are diseased at and around a bifurcation with a straight stent, the unstented side region between the main vessel and the branch vessel to be treated can be excessive, or an excessive projection into the main vessel portion can result, if the stent can not be positioned accurately and precisely near the ostium of the branch vessel being treated.

Figure 1:
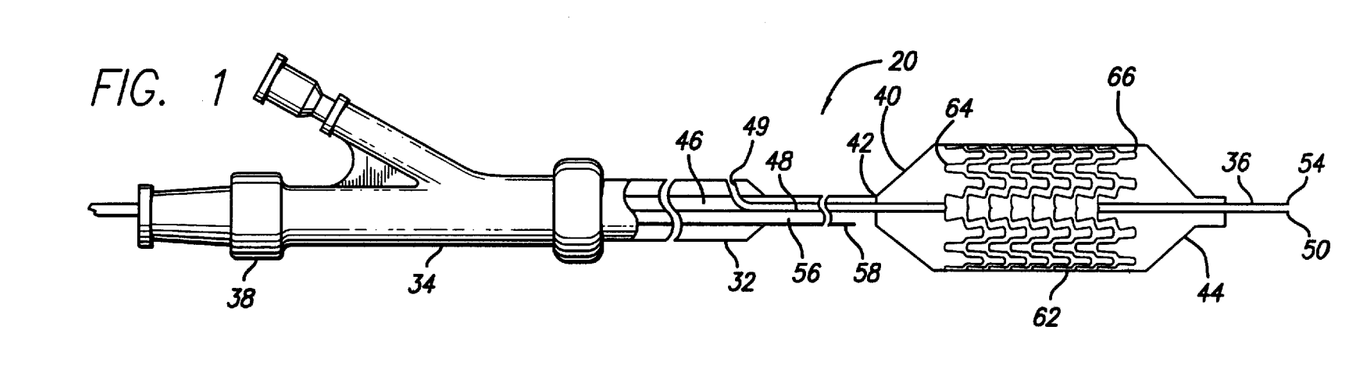
FIG. 1 is a schematic diagram of an ostial placement catheter assembly according to a first embodiment of the invention.

As is illustrated in the drawings, in order to improve the accuracy and decreased variability in positioning of a straight therapeutic device such as a straight stent at an ostium of a bifurcation, the invention is accordingly embodied in a catheter assembly for placement of a therapeutic device for treatment of a patient's bifurcated body lumen such as a bifurcated blood vessel having a main vessel portion, a plurality of branch vessels extending from the main vessel portion, and a vessel carina between the branch vessels, and a method for placement of the therapeutic device utilizing the catheter assembly of the invention. With reference to FIGS. 1 and 2, in one currently preferred embodiment, the present invention provides for an ostial placement catheter assembly 20 for placement of a therapeutic device in a side branch of a bifurcated body lumen 22, such as a blood vessel having a trunk or main vessel portion 24, a first or target side branch vessel 26, and one or more second branch vessels 28 such as a main branch vessel connected to the main vessel portion adjacent to a carina 30 of the bifurcation between the branch vessels.

The catheter assembly includes a placement catheter shaft 32, having a proximal end 34 and a leading edge distal end 36, with an over-the-wire adapter hub 38 typically provided at the proximal end of the placement catheter. An expandable member, such as a dilatation balloon 40, having a proximal end 42 and a distal end 44, is typically mounted adjacent to the distal end of the placement catheter shaft. The placement catheter includes a lumen 46, in fluid communication with the expandable member, and typically extending to the proximal end of the catheter and to the adapter hub, for inflation and deflation of the expandable member. The placement catheter also includes a tracking guide wire lumen 48, with a guide wire entry port 49, and a first guide member exit port 50 for a tracking guide wire 52, such as a rapid exchange tracking guide wire or an over the wire style guide wire, for example, which is placed in the branch in which the therapeutic device is to be placed. The placement catheter also includes a distal soft tip 54, and a positioning guide member lumen 56 typically extending to the proximal end of the placement catheter and to the adapter hub, with a second guide member exit port 58 on the placement catheter shaft adjacent to the proximal end of the balloon, for a positioning guide member such as an over-the-wire positioning guide member 60. The positioning guide member is currently preferably a metal guide wire, but may also be an elongated member formed of nylon, Teflon, HDPE, and the like. A therapeutic device 62, having a proximal end 64 and a distal end 66, is preferably mounted on the expandable member, such as by crimping the therapeutic device on the expandable member. The therapeutic device may be a graft or stent, for example, that can have virtually any pattern known from prior art grafts and stents, and may be made of a suitable biocompatible material such as stainless steel, titanium, tantalum, super-elastic nickel-titanium (NiTi) alloys, and polymeric materials, for example, and similar suitable materials such as are known to those skilled in the art.

Referring to FIG. 2, the two guide wires are used to position the delivery system at the ostium of a vessel. The therapeutic device is mounted on the expandable member for placement in a target branch vessel, and the distal end of the tracking guide wire is placed into the target branch vessel. The placement catheter is then introduced over the tracking guide wire through the tracking guide wire lumen, and the positioning guide member is introduced through the positioning guide member lumen and extending the distal end of the positioning guide member through the exit port and is positioned in a remaining branch vessel. The distal end of the positioning guide member is placed in another vessel branching from the ostium of the target branch vessel, such as in the main branch vessel, for example. The exit port for the positioning guide member is optimally located in the catheter proximal to the position of the therapeutic device on the expandable member and the therapeutic device mounted on the expandable member, to assure accuracy in delivery of the therapeutic device, and may partially overlay the expandable member. The positioning guide member preferably exits the catheter shaft just proximal to the position of the therapeutic device on the expandable member, thus forming an intersection of the positioning guide member and the catheter shaft, which allows accurate positioning of the stent at the ostium by accurate mating of the intersection of the positioning guide member and the catheter shaft with the vessel carina. Alternatively, the positioning guide member may exit the catheter shaft partially in a manner so as to partially overlay the expandable member. The placement catheter is then advanced distally in the main vessel until the positioning guide member engages the vessel carina between the branch vessels. The mechanical stop as the positioning guide member engages the vessel carina can typically be felt by the practitioner, and the therapeutic device is then placed in the target branch vessel, such as by expanding the expandable member to lodge the therapeutic device in the target branch vessel.

Figure 3:
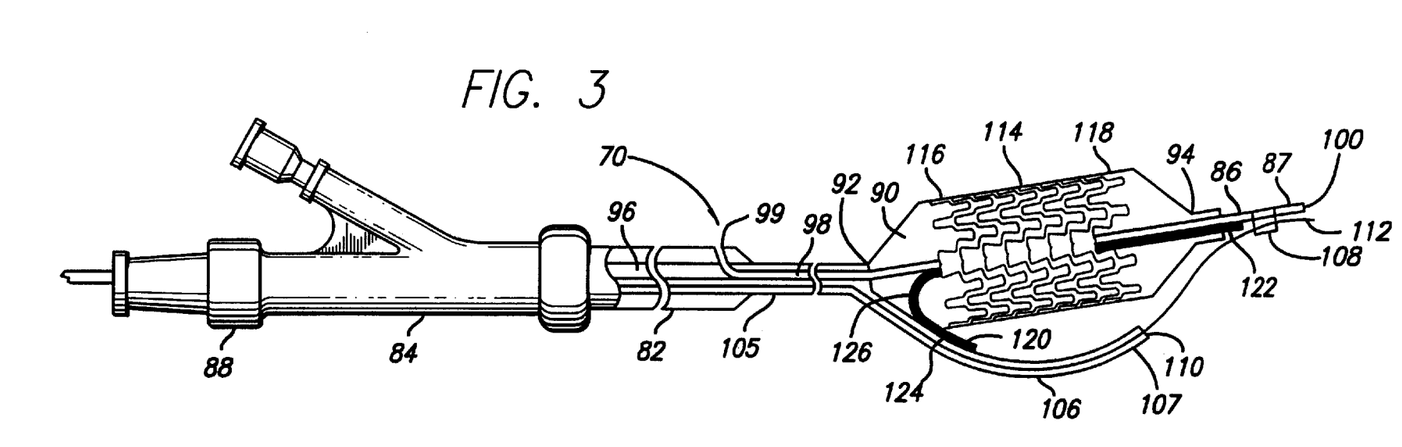
FIG. 3 is a schematic diagram of an ostial placement catheter assembly according to a second embodiment of the invention showing the secondary catheter member coupled to the placement catheter.
Figure 4:
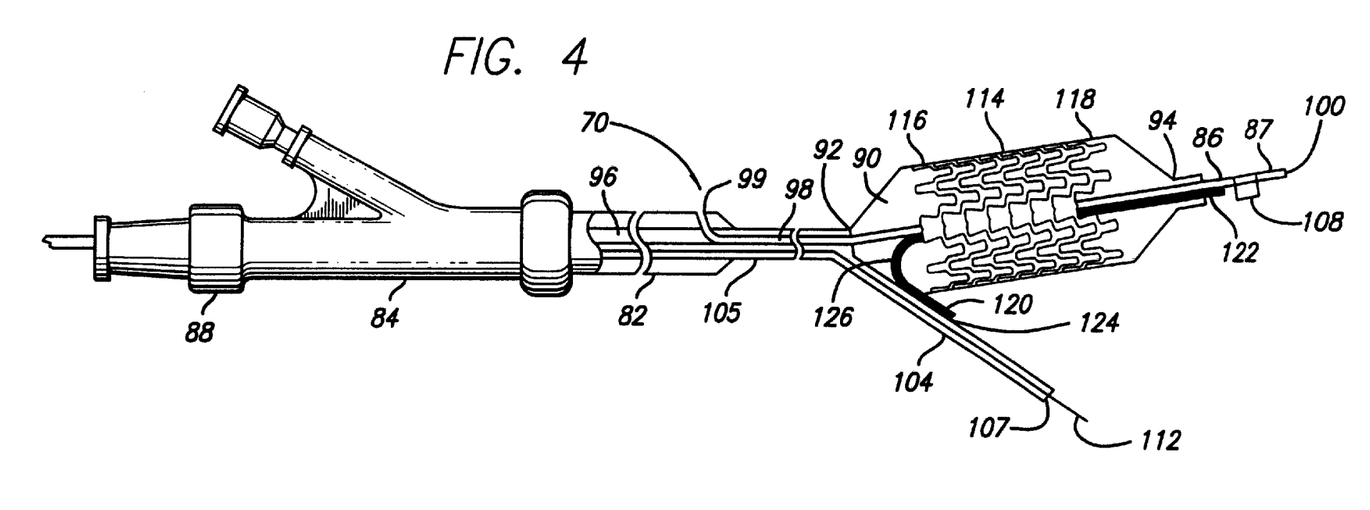
FIG. 4 is a schematic diagram of the ostial placement catheter assembly of FIG. 3, showing the secondary catheter member uncoupled from the placement catheter.

With reference to FIGS. 3, 4, and 5, in a second presently preferred embodiment, the invention provides for an ostial placement catheter assembly 70 for placement of a therapeutic device such as a graft or a stent, in a branch of a bifurcated body lumen 72, such as a blood vessel having a trunk or main vessel portion 74, a first or target side branch vessel 76, and one or more second branch vessels 78 such as a main branch vessel connected to the main vessel portion adjacent to a carina 80 of the bifurcation between the main vessel portion and the branch vessels. The catheter assembly includes a placement catheter shaft 82, having a proximal end 84 and a distal end 86, with a first leading edge distal tip 87 at the distal end, and an over-the-wire attachment hub 88 at the proximal end of the placement catheter. An expandable member such as a dilatation balloon 90, having a proximal end 92 and a distal end 94, is preferably mounted onto the distal end of the placement catheter shaft. The placement catheter includes a lumen 96, in fluid communication with the expandable member, and typically extending to the proximal end of the placement catheter and to the adapter hub, for inflation and deflation of the expandable member. The placement catheter also includes a tracking guide wire lumen 98, with a guide wire entry port 99, and a first guide member exit port 100 for a tracking guide wire 102, such as a rapid exchange tracking guide wire or an over the wire style guide wire, for example, which is placed in the branch in which the therapeutic device is to be placed.

The second embodiment of the catheter assembly also includes a secondary catheter member 104, having a positioning guide member lumen 106 within the secondary catheter member, connected in fluid communication with a positioning guide member lumen 105 in the placement catheter shaft typically extending to the proximal end of the placement catheter, and to the adapter hub, and a second leading edge distal tip 107. The secondary catheter member is preferably attached to the distal portion of the shaft adjacent to the proximal end of the expandable member. The second leading edge distal tip of the secondary catheter member is typically placed in the altenate branch or main branch vessel not being treated, and provides a support for creation of the mechanical stop for the placement catheter. The first leading edge distal tip is typically longer than the second leading edge distal tip. Means 108 are also provided for coupling the secondary catheter member to the distal end of the placement catheter, distal to the expandable member, such as an annular coupling member defining an opening adapted to receive the positioning guide member, and from which the positioning guide member or another separate elongated coupling member can be inserted and withdrawn by the practitioner, for coupling and uncoupling the secondary catheter member from the first leading edge distal tip as is shown in FIG. 3, for deployment in the alternate or main branch that is not being treated. Alternatively, the means for coupling can be a short flexible section of dual lumen extending from the catheter shaft proximal to the first leading edge distal tip, connecting the shorter secondary catheter member to the leading edge distal tip of the placement catheter while the first leading edge distal tip is maneuvered to the bifurcation site.

A second guide wire exit port 110, connected in communication with the positioning guide member lumen adjacent to the proximal end of the balloon, is provided at the end of the second leading edge distal tip of the secondary catheter member, for a positioning guide member such as an over-the-wire positioning guide member 112. The positioning guide member is currently preferably a metal guide wire, but may also be an elongated member formed of nylon, Teflon, HDPE, and the like. A therapeutic device 114 such as a straight stent, having a proximal end 116 and a distal end 118, is preferably mounted on the expandable member, such as by crimping the therapeutic device on the expandable member. An elongated angle member 120, having the shape of a two pronged, J-shaped stirrup, is also advantageously provided for engaging the carina of the bifurcation to be treated. The elongated angle member is currently preferably made of a nylon material, although the elongated angle member may also be made of polyamide block copolymers, such as those available from Elf Atochem under the brand name "PEBAX", or other similar suitable materials. The elongated angle member has a distal end 122 forming a first prong disposed near the distal end of the first leading edge distal tip 87, and a proximal end 124 forming a second prong attached near the distal end of the secondary catheter member. The first and second prongs are joined together by a curved intermediate arch section 126, located near the proximal end of the therapeutic device. The proximal end 124, the second prong, of the elongated angle member is preferably attached adjacent to the distal end of the secondary catheter member, typically by an adhesive such as a cyanoacrylate adhesive for example, available from Loctite Corporation, although other similar adhesives, and other means of attachment such as solvent bonding, heat bonding or welding, and the like, may also be suitable. The distal end 122, the first prong, of the elongated angle member is adapted to extend between and to be secured to the catheter by the therapeutic device, between the therapeutic device and the expandable member, so as to form the arch section in the elongated angle member between the ends of the elongated angle member proximal to the therapeutic device. The first prong of the elongated angle member may optionally be attached to the first leading edge distal tip of the placement catheter, such as by adhesive or other means as noted above.

It should be appreciated that alternatively, a secondary catheter member for a positioning guide member may also be retracted and advanced through the second guide member port. It should also be understood that the invention may also be used for placement of a self-expanding stent that is introduced in a collapsed state, and can be allowed to expand into position without the need for the use of an expandable member, once the self-expanding stent is properly positioned. It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A catheter assembly for placement of a therapeutic device for treatment of a patient's bifurcated body lumen having a main vessel portion, a plurality of branch vessels extending from the main vessel portion, and a vessel carina between the branch vessels, comprising:

a placement catheter having a proximal end and a distal end, the placement catheter being adapted for mounting a therapeutic device at a location proximal to the distal end of the placement catheter, and for delivery of the therapeutic device in one of the branch vessels, the placement catheter including an expandable member mounted to the placement catheter adjacent to the distal end of the placement catheter, the placement catheter including means for inflating and deflating the expandable member, and the expandable member being adapted for mounting and delivery of the therapeutic device in one of the branch vessels;

a tracking guide wire lumen disposed and extending within at least a portion of the placement catheter, the tracking guide wire lumen adapted to receive a tracking guide wire for slidable movement within the tracking guide wire lumen; and a positioning guide member lumen disposed and extending within at least a portion of the placement catheter and having an exit port in the catheter, the exit port being toward the proximal end and adjacent to a central location of the expand member on the placement catheter, the positioning guide member lumen adapted to receive a positioning guide member for slidable movement within the positioning guide member lumen.

2. The catheter assembly of claim 1, wherein the placement catheter comprises an adapter hub.

3. A catheter assembly for placement of a therapeutic device for treatment of a patient's bifurcated body lumen having a main vessel portion, a plurality of branch vessels extending from the main vessel portion, and a vessel carina between the branch vessels, comprising:

a placement catheter having a proximal end and a distal end, the placement catheter being adapted for mounting a therapeutic device at a location proximal to the distal end of the placement catheter, and for delivery of the therapeutic device in one of the branch vessels;

a tracking guide wire lumen disposed and extending within at least a portion of the placement catheter, the tracking guide wire lumen adapted to receive a tracking guide wire for slidable movement within the tracking guide wire lumen;

a positioning guide member lumen disposed and extending within at least a portion of the placement catheter and having an exit port in the placement catheter, the exit port being toward the proximal end and adjacent to a central location of the therapeutic device on the placement catheter, the positioning guide member lumen adapted to receive a positioning guide member for slidable movement within the positioning guide member lumen;

a secondary catheter member having a distal end and a proximal end, the secondary catheter member mounted to the placement catheter and including a positioning guide member lumen connected in communication with the positioning guide member lumen of the placement catheter, the positioning guide member lumen of the secondary catheter member adapted to receive the positioning guide member for slidable movement within a positioning guide member lumen of the secondary catheter member;

means for coupling and uncoupling the distal end of the secondary catheter member from the distal end of the placement catheter distal to the location of the therapeutic device; and an elongated angle member having a distal end and a proximal end, the elongated angle member mounted to the secondary catheter member and adapted to be retained by the therapeutic device and extending between the therapeutic device and the location of the therapeutic device so as to form an arch in the elongated angle member between the distal and proximal ends of the elongated angle member proximal to the therapeutic device.

4. The catheter assembly of claim 3, wherein the means for coupling and uncoupling comprises an annular coupling member adapted to receive the distal end of the positioning guide member.

5. The catheter assembly of claim 3, wherein one end of the elongated angle member is mounted adjacent to the distal end of the secondary catheter member.

6. A catheter assembly for placement of a therapeutic device for treatment of a patient's bifurcated body lumen having a main vessel portion, a plurality of branch vessels extending from the main vessel portion, and a vessel carina between the branch vessels, comprising:

a catheter having a proximal end and a distal end, the catheter being adapted for mounting a therapeutic device at a location proximal to the distal end of the catheter, and for delivery of the therapeutic device in a target branch vessel;

a tracking guide wire lumen disposed and extending within at least a portion of the catheter, the tracking guide wire lumen adapted to receive a tracking guide wire for slidable movement within the tracking guide wire lumen;

a positioning guide member lumen disposed and extending within at least a portion of the catheter and having an exit port in the catheter proximal to the location of the therapeutic device, the positioning guide member lumen adapted to receive a positioning guide member for slidable movement within the positioning guide member lumen;

a secondary catheter member having a distal end and a proximal end, the secondary catheter member mounted to the placement catheter and including a positioning guide member lumen connected in communication with the positioning guide member lumen of the placement catheter, the positioning guide member lumen of the secondary catheter member adapted to receive the positioning guide member for slidable movement within the positioning guide member lumen of the secondary catheter member;

means for coupling and uncoupling the distal end of the secondary catheter member from the distal end of the placement catheter distal to the location of the therapeutic device; and an elongated angle member having a distal end and a proximal end, the elongated angle member mounted to the secondary catheter member and adapted to be retained by the therapeutic device and extending between the therapeutic device and the secondary catheter so as to form an arch in the elongated angle member between the distal and proximal ends of the elongated angle member proximal to the therapeutic device.

7. The catheter assembly of claim 6, wherein the catheter comprises an expandable member mounted adjacent to the distal end of the placement catheter, the catheter including means for inflating and deflating the expandable member, the expandable member being adapted for mounting and delivery of the therapeutic device in a target branch vessel, and wherein the exit port in the placement catheter is located proximal and adjacent to a main body location of the expandable member.

8. The catheter assembly of claim 6, wherein the placement catheter comprises an adapter hub.

9. The catheter assembly of claim 6, wherein the means for coupling and uncoupling comprises an annular coupling member adapted to receive the distal end of the positioning guide member.

10. The catheter assembly of claim 6, wherein one end of the elongated angle member is mounted adjacent to the distal end of the secondary catheter member.

11. A method for placement of a therapeutic device for treatment of a patient's bifurcated body lumen having a main vessel portion, a plurality of branch vessels extending from the main vessel portion, and a vessel carina between the branch vessels, comprising the steps of:

providing a placement catheter having a proximal end and a distal end, the placement catheter having an expandable member mounted to the distal end of the placement catheter, a tracking guide wire lumen disposed and extending within at least a portion of the placement catheter, and a positioning guide member lumen disposed and extending within at least a portion of the placement catheter and having an exit port in the catheter proximal and adjacent to main body location of the expandable member;

mounting a therapeutic device on the expandable member for placement in a target branch vessel;

placing a distal end of a tracking guide wire into the target branch vessel;

introducing the placement catheter over the tracking guide wire through the tracking guide wire lumen;

introducing a positioning guide member through the positioning guide member lumen and extending a distal end of the positioning guide member through the exit port in the catheter proximal to the expandable member;

placing the distal end of the positioning guide member in another branch vessel;

advancing the placement catheter distally in the main vessel portion until the positioning guide member engages the vessel carina between the branch vessels; and placing the therapeutic device in a target branch vessel.

12. A method for placement of a therapeutic device for treatment of a patient's bifurcated body lumen having a main vessel portion, a plurality of branch vessels extending from the main vessel portion, and a vessel carina between the branch vessels, comprising the steps of:

providing a placement catheter having a proximal end and a distal end, the placement catheter having a therapeutic device mounted thereon, a tracking guide wire lumen disposed and extending within at least a portion of the placement catheter, a positioning guide member lumen disposed and extending within at least a portion of the placement catheter and having an exit port in the catheter proximal to the therapeutic device mounted on the placement catheter, a secondary catheter member having a distal end and a proximal end, the secondary catheter member mounted to the placement catheter and including a positioning guide member lumen connected in communication with the positioning guide member lumen of the placement catheter, and an elongated angle member having a distal end and a proximal end, the elongated angle member mounted to the secondary catheter member and adapted to be retained by the therapeutic device and extending between the therapeutic device and the placement catheter so as to form an arch in the elongated angle member between the distal and proximal ends of the elongated angle member proximal to the therapeutic device;

placing the distal end of a tracking guide wire into a main vessel portion of a target branch vessel;

coupling the distal end of the secondary catheter member to the distal end of the placement catheter distal to the therapeutic device mounted on the placement catheter;

introducing the placement catheter over the tracking guide wire using the tracking guide wire lumen;

introducing a positioning guide member through the positioning guide member lumen and extending the distal end of the positioning guide member through the exit port in the placement catheter proximal to the therapeutic device mounted on the placement catheter;

uncoupling the distal end of the secondary catheter member from the distal end of the placement catheter distal to the therapeutic device mounted on the placement catheter;

placing the distal end of a positioning guide member disposed in the positioning guide member lumen in another branch vessel;

advancing the placement catheter distally in the main vessel portion until the arch of the elongated angle member engages the vessel carina between the branch vessels; and placing the therapeutic device in the target branch vessel.

13. The method of claim 12, wherein the placement catheter comprises an expandable member adjacent to the distal end of the placement catheter, and the therapeutic device is mounted on the expandable member.

14. The method of claim 13, wherein the distal end of the placement catheter distal to the expandable member includes an annular coupling member adapted to receive the distal end of the positioning guide member, and wherein a step of coupling the distal end of the secondary catheter member to the distal end of the placement catheter comprises placing the distal end of the positioning guide member in the annular coupling member.

15. The method of claim 14, wherein a step of uncoupling the distal end of the secondary catheter member from the distal end of the placement catheter comprises withdrawing the distal end of the positioning guide member from the annular coupling member.

* * * * *

UNITED STATES PATENT AND TRADEMARK OFFICE
CERTIFICATE OF CORRECTION

PATENT NO. : 6,544,219 B2
DATED : April 8, 2003
INVENTOR(S) : Dorrie M. Happ et al.

It is certified that error appears in the above-identified patent and that said Letters Patent is hereby corrected as shown below:

Title page,
Item [56], References Cited, FOREIGN PATENT DOCUMENTS, 5th listed patent, change "FR 0 673 843 9/1992", to read -- FR 2 673 843 9/1992 --.

Column 10,
Line 45, change "catheter proximal and adjacent to', to read -- catheter, the exit port being toward the proximal end and adjacent to a central location of the --.

Signed and Sealed this

Ninth Day of September, 2003

JAMES E. ROGAN
*Director of the United States Patent and Trademark Office*